US006391888B1

(12) United States Patent
Gleich

(10) Patent No.: US 6,391,888 B1
(45) Date of Patent: May 21, 2002

(54) TOPICAL ANESTHETICS USEFUL FOR TREATING CANCER

(75) Inventor: Gerald J. Gleich, Rochester, MN (US)

(73) Assignees: Mayo Foundation for Medical Education and Research, Rochester, MN (US); Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/687,389

(22) Filed: Oct. 13, 2000

Related U.S. Application Data
(60) Provisional application No. 60/159,877, filed on Oct. 15, 1999.

(51) Int. Cl.$^7$ .............................................. A61K 31/44
(52) U.S. Cl. ..................... 514/304; 514/626; 514/351; 514/535; 514/312; 514/315; 514/338; 514/408
(58) Field of Search ................................ 514/304, 626, 514/351, 535, 312, 315, 338, 408

(56) References Cited

U.S. PATENT DOCUMENTS

| | | | |
|---|---|---|---|
| 4,181,725 A | | 1/1980 | Voorhees et al. ............ 424/258 |
| 5,331,013 A | | 7/1994 | Ahlman et al. ............. 514/626 |
| 5,510,339 A | * | 4/1996 | Gleich et al. ................ 514/171 |
| 5,631,267 A | * | 5/1997 | Gleich et al. ................ 514/312 |
| 5,837,713 A | | 11/1998 | Gleich ......................... 514/312 |
| 6,071,910 A | | 6/2000 | Gleich et al. ............. 514/235.5 |

FOREIGN PATENT DOCUMENTS

| | | | |
|---|---|---|---|
| EP | 0643964 | 3/1995 | .......... A61K/31/16 |
| JP | 56075432 | 6/1981 | .......... A61K/31/445 |
| WO | 93/17674 | 9/1993 | .......... A61K/31/165 |
| WO | 94/18972 | 9/1994 | .......... A61K/31/44 |
| WO | 99/51565 | 10/1999 | .......... C07C/233/04 |
| WO | 00/72853 | 12/2000 | .......... A61K/33/22 |

OTHER PUBLICATIONS

Jones, E.W., et al., "Cytotoxic Effects of membrane–Active Agents in Human Leukaemia Cell Lines", *Biochem. Soc. Trans.*, 23 (1), p. 27S, (1995).

Qin, Y., et al., "Dexniguldipine hydrochloride inhibits growth of human HT–29 colon carcinoma cells and expression of protein kinase C Δ and ζ", *Int'l J. of Onocology*, 7(5), pp. 1073–1077, (1995).

Sakurai, M., et al., "Positive symptoms in multiple sclerosis: their treatment with sodium channel blockers, lidocaine and mexiletine", *J. of Neurological Sciences*, 162 (2), pp. 162–168, (Jan. 15, 1999).

Schaub, R.G., et al., "Reduction of ischemic myoardial damage in the dog by lidocaine infusion", *Amer. J. of Pathology*, 87(2), pp. 339–414, (1977).

Strasser, R.H., et al., "Two Distinct Mechanisms Mediate a Differential Regulation of Protein Kinase C Isozymes in Acute and Prolonged Myocardial Ischemia", *Circulation Research*, 85, pp. 77–87, (1999).

Tomoda, M.K., et al., "Lidocaine Inhibits Stimulation–Coupled Responses of Neutrophils and Protein Kinase C Activity", *Physiological Chemistry and Physics*, 22 (4), pp. 199–210, (1990).

Trudell, J.R., et al., "Inhibition of protein kinase C by Local Anesthetics", *Annals of the NY Academy of Sciences*, pp. 743–746, (1991).

Vrăbiescu, A., et al., "Analysis by flow cytometry of the subpopulations of lymphocytes from the peripheral blood of procain or diethylaminoethanol treated rabbits", *Rom. Arch. Microbiol. Immunol.*, 57 (2), pp. 111–124, (Apr. 1998).

Weisenthal, L.M., et al., "Perturbation of In Vitro Drug Resistance in Human Lymphatic Neoplasms by Combinations of Putative Inhibitors of Protein Kinase C", *Cancer Treatment Reports*, 71 (12), pp. 1239–1243, (Dec. 1987).

\* cited by examiner

*Primary Examiner*—James H. Reamer
(74) *Attorney, Agent, or Firm*—Schwegman, Lundberg, Woessner & Kluth, P.A.

(57) ABSTRACT

The invention provides methods which are useful for treating diseases (e.g., cancer) where PKCδ is implicated, and modulation (e.g, inhibition) of its activity is desired.

16 Claims, No Drawings

TOPICAL ANESTHETICS USEFUL FOR TREATING CANCER

PRIORITY OF INVENTION

This application claims priority of invention under 35 U.S.C. §119(e) from U.S. Provisional Application No. 60/159,877, filed Oct. 15, 1999.

GOVERNMENT FUNDING

The invention described herein was made with U.S. Government support under Grant Number AI-34577 awarded by the National Institutes of Health. The United States Government has certain rights in the invention.

BACKGROUND OF THE INVENTION

Protein kinases play a critical role in cellular development, differentiation and transformation. One of the largest gene families of non-receptor serine-threonine protein kinases is protein kinase C (PKC). Since the discovery of PKC more than a decade ago, a multitude of physiological signaling mechanisms have been ascribed to the enzyme.

The PKC gene family consists presently of 11 genes which are divided into four subgroups: 1) classical PKC$\alpha$, $\beta_1$, $\beta_2$ and $\gamma$, 2) novel PKC$\delta$, $\epsilon$, $\eta$, and $\theta$, 3) atypical PKC$\zeta$, $\lambda$, $\eta$ and $\iota$ and 4) PKC$\mu$. Because of their unique structural features, diverse PKC isoforms are thought to have highly specialized roles in signal transduction in response to physiological stimuli, as well as in neoplastic transformation and differentiation. The $\alpha$, $\beta_1$, $\beta_2$ and $\gamma$ isoforms are $Ca^{2+}$, phospholipid- and diacylglycerol-dependent and represent the classical isoforms of PKC, whereas the other isoforms are activated by phospholipid and diacylglycerol but are not dependent on $Ca^{2+}$.

From a pharmacological perspective, the PKC isozymes are an exciting target for cancer therapy, as well as for other diseases such as autoimmune diseases, ischemia, and inflammatory diseases (see D. Leszczynski, *The Cancer Journal*, The role of protein kinase C in regulation of apoptosis: a brief overview of the controversy, 9, number 6, (November–December 1996); R. H. Strasser, et al., *Circulation Research*, 1999, 85, 1, 77–87). There is also considerable interest in identifying agents that possess selectivity for one or more isozymes, since selective agents may have fewer side effects than agents that act on multiple PKC isozymes.

U.S. Pat. Nos. 5,510,339 and 5,631,267 disclose the use of topical anesthetics to treat bronchial asthma and other eosinophil associated hypersensitivity diseases. Additionally, U.S. Pat. No. 5,837,713 discloses the use of a synergistic combination of a topical anesthetic and a glucocorticoid to treat eosinophil associated pathologies.

U.S. patent application Ser. No. 08/985,613 discloses the use of a sulfonylurea receptor (SUR) binding agent to treat IL-5 mediated pathologies. The application also discloses a method for inhibiting cytokine-induced eosinophil survival or activation with a sulfonylurea receptor binding agent, optionally in combination with one or more topical anesthetics and/or glucocorticoids. The application also discloses a method for treating a disease mediated by IL-5 with an agent that is able to modify (e.g. block) ATP-dependent potassium channels, or a protein with which an ATP-dependent potassium channel interacts (such as a SUR).

Additionally, M. K. Tomoda et al., *Physiol. Chem. Phys. & Med. NMR*, 1990, 22, 199–210, disclose data suggesting that lidocaine inhibits calcium-activated, phospholipid-dependent protein kinase (PKC); and L. M. Weisenthal et al., *Cancer Treatment Reports*, 1987, 71, 1239–1243, disclose data suggesting that lidocaine, in combination with one or more other specific agents described therein, may be useful to circumvent acquired drug resistance in HLN. However, L. M. Weisenthal et al. also disclose that local anesthetic agents by themselves have not been confirmed to have activity in clinical human cancer.

Despite the above disclosures, there is a continuing need for novel compounds which can modulate PKC. In particular, there is a need for compounds that are selective for one or more PKC isotypes (e.g. PKC$\delta$). Such compounds may be useful, for example, to treat cancer or autoimmune diseases, as well as other diseases that are effected by the activity of PKC$\delta$.

SUMMARY OF THE INVENTION

In the course of studying the mechanism by which topical anesthetics inhibit cytokine mediated eosinophil survival, applicant discovered that lidocaine binds to and modulates (e.g. inhibits) the effects of the calcium independent PKC isozyme PKC$\delta$. Thus, applicant has discovered that lidocaine and other topical anesthetics are useful agents for treating diseases wherein PKC$\delta$ is implicated, and modulation (e.g. inhibition) of its activity is desired.

Accordingly, the invention provides a therapeutic method for treating a disease or condition characterized by the pathological proliferation of mammalian cells, comprising administering to a mammal in need of such therapy, an amount of a topical anesthetic, or a pharmaceutically acceptable salt thereof, effective to treat the disease or condition.

The invention also provides a therapeutic method for treating an autoimmune disease comprising administering to a mammal in need of such therapy, an amount of a topical anesthetic, or a pharmaceutically acceptable salt thereof, effective to treat the autoimmune disease.

The invention also provides a method to inhibit the activity of PKC$\delta$ in vitro comprising contacting PKC$\delta$ with an effective inhibitory amount of a topical anesthetic; or a salt thereof. Such a method is useful as a pharmacological tool to further investigate the actions of PKC$\delta$, or to identify agents possessing selectivity for one or more PKC isozymes.

The invention also provides a therapeutic method for inhibiting the activity of PKC$\delta$ in a mammal in need of such therapy comprising administering to the mammal, an effective PKC$\delta$ inhibitory amount of a topical anesthetic; or a pharmaceutically acceptable salt thereof.

The invention also provides a method for treating a condition or disease in a mammal wherein the activity of PKC$\delta$ is implicated and antagonism of its action is desired comprising administering to the mammal, an amount of a topical anesthetic, or a pharmaceutically acceptable salt thereof, effective to inhibit PKC$\delta$ so as to treat the condition or disease.

The invention also provides the use of a therapeutically effective amount of a topical anesthetic; or a pharmaceutically acceptable salt thereof for the manufacture of a medicament for the treatment of a disease wherein PKC$\delta$ is implicated and modulation of its activity is desired (e.g. cancer, an autoimmune disease, ischemia, or an imflammatory disease).

In the therapeutic methods of the invention, a topical anesthetic or a pharmaceutically acceptable salt thereof can be administered in combination with one or more other therapeutically active agents (e.g. chemotherapeutic agents), or can be administered alone (as the sole therapeutically active agent for treating a given disease).

DETAILED DESCRIPTION OF THE INVENTION

Autoimmune diseases are diseases that are characterized by the presence of autoreactive T lymphocytes resulting in pathological inflammation and subsequent damage or destruction of target tissue. A number of autoimmune diseases are known in the art, including rheumatoid arthritis, multiple sclerosis, lupus, and late-onset diabetes.

Topical anesthetics, all of which are believed to be useful in the present invention, are an art-recognized class of drugs which temporarily interrupt mammalian nerve transmissions. They can generally be grouped into two chemical classifications structurally; the N-arylamides or carboxamides, such as lidocaine; and the aminoalkylbenzoates, such as procaine, benoxinate and proparacaine. Preferred N-arylamides comprise the N—($C_7$–$C_{22}$)arylamides of amino-substituted ($C_1$–$C_5$) carboxylic acids, e.g., N-[(mono or di-($C_1$–$C_4$)alkyl)phenyl] amides of aliphatic ($C_1$–$C_5$)carboxylic acids, which acids are preferably substituted with the moiety (R)($R^1$)N— wherein R is H or ($C_1$–$C_5$)alkyl and $R^1$ is ($C_1$–$C_5$)alkyl. For example, a preferred carboxylic acid can have the general formula (R)($R^1$)N(X)$CO_2$H where R and $R^1$ are as defined above and X is a branched- or straight-chain ($C_1$–$C_5$) alkylene group such as 1,1-ethylene, 1,2-ethylene, methylene, 2,2-propylene, 1,3-propylene, and the like. Another preferred class of N-arylamides are the N-[(mono- or di-($C_1$–$C_4$)alkyl)phenyl]amides of 5- or 6-membered-heterocycloaliphatic carboxylic acids, which acids comprise one or two [($C_1$–$C_4$)alkyl-substituted]N atoms, i.e., N-butylpiperidine-2-carboxylic acid.

The aminoalkylbenzoates include esters between benzoic acids and alcohols of the general formula ($R^4$)($R^5$)N(X)OH, wherein X is as defined above, $R^4$ is H or ($C_1$–$C_4$)-alkyl, $R^5$ is ($C_1$–$C_4$)alkyl or $R^4$ and $R^5$ taken together with N are a 5- or 6-membered heterocycloaliphatic ring, optionally substituted by ($C_1$–$C_3$)alkyl or comprising an additional ring O- or N-atom. The benzoic acid moiety can be the moiety ($R^2$)($R^3$) Ar$CO_2$H wherein Ar is an aromatic —$C_6H_3$—radical "phenylene" and (phenylene) and each $R^2$ and $R^3$ is H, halo, preferably Cl, ($R^5$)(H)N—, $H_2$N— or ($C_1$–$C_5$)alkoxy.

Useful topical anesthetics include lidocaine ((2-diethylamino)-N-(2,6-dimethylphenyl)-acetamide) (see Lofgren et al. (U.S. Pat. No. 2,441,498), May & Baker (British Patent No. 706409) and Macfarlane & Co. (British Patent No. 758,224)); bupivacaine (1-butyl-N-(2,6-dimethylphenyl)-2-piperidinecarboxyamide) (see Thuresson et al., (U.S. Pat. No. 2,955,111) and Sterling Drug (British Patent Nos. 1,166,802 and 1,180,712)); mepivacaine (2-piperidinecarboxyamide, N-(2,6-dimethylphenyl)-1-methyl), chloroprocaine (4-amino-2-chlorobenzoic acid 2-(diethylamino)ethyl ester); procaine (4-aminobenzoic acid 2-(diethylamino)ethyl ester); etidocaine (N-(2,6-dimethylphenyl)-2-(ethylpropylamino)butanamide; see, Astra (German Patent No. 2162744)); tetracaine (4-(butylamino)benzoic acid 2-(dimethylaminoethyl ester; see Shupe (U.S. Pat. No. 3,272,700)); benoxinate (4-amino-3-butoxybenzoic acid 2-(diethylamino)ethyl ester (U.K. Patent No. 654,484)) proparacaine (3-amino-4-propoxybenzoic acid 2-(diethylamino) ethyl ester); dibucaine (3-butoxy-N-[2-(diethylamino)ethyl]-4-quinolinecarboxyamide; Miescher (U.S. Pat. No. 1,825,623)); dyclonine (1-(4-butoxyphenyl)-3-(1-piperidinyl-1-propanone)); isobucaine (1-propanol, 2-methyl-2-[(2-methylpropyl)amino]benzoate; meprylcaine ([(2-methyl)(2-propylamino)propyl]benzoate); piperocaine ((2-methylpiperidin-1-ylpropyl(benzoate)); prilocaine (N-(2-methylphenyl)-2-(propylamino) propanamide); propoxycaine (2-(diethylamino)ethyl-([2'-methyl-4-amino]benzoate)); pyrrocaine (1-(pyrrolidin-1-yl)-N-(2,6-dimethylphenyl)acetamide, butacaine (((3-dibutylamino)propyl)-(2'-aminobenzoate)); cyclomethylcaine (((3-(2'methylproperidine-1-yl))propyl)-[4'-cyclohexyloxy-benzoate]); dimethyisoquin, diperodon, hexylcaine ((([(2-cyclohexylamino)(1-methyl)]ethyl) (benzoate); proparacaine (((2-diethylamino)ethyl) [(4'-propyloxyl-3'-amino)benzoate]); cocaine and its analogs (see, Carroll et al., *J. Med. Chem.*, 34, 2719 (1991); *Eur. J. Pharmacol.*, 184, 329 (1990); and the pharmaceutically acceptable salts thereof.

These topical anesthetics and the salts thereof are discussed in detail in *Remington's Pharmaceutical Sciences*, A. Osol, ed., Mack Pub. Co., Easton, Pa. (16th ed. 1980), and in *The Merck Index* (11th ed. 1989). Preferred salts include the amine addition salts of inorganic and organic acids, e.g., the hydrochloride, hydrobromide, sulfate, oxalate, fumarate, citrate, malate, propionate and phosphate salts. The hydrochloride and sulfate salts are preferred for use in the present invention.

The following definitions are used, unless otherwise described. Halo is fluoro, chloro, bromo, or iodo. Alkyl denotes both straight and branched groups; but reference to an individual radical such as "propyl" embraces only the straight chain radical, a branched chain isomer such as "isopropyl" being specifically referred to.

It will be appreciated by those skilled in the art that topical anesthetics having one or more chiral center(s) may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase) and how to determine the ability of a compound to modulate the activity of PKCδ using assays that are known in the art.

Specific and preferred values listed below for radicals, substituents, and ranges, are for illustration only; they do not exclude other defined values or other values within defined ranges for the radicals and substituents.

Specifically, ($C_1$–$C_5$)alkyl can be methyl, ethyl, propyl, isopropyl, butyl, iso-butyl, sec-butyl, pentyl, or 3-pentyl.

In cases where a topical anesthetic is sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The topical anesthetics can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Single dosages for injection, infusion or ingestion will generally vary between about 10–1500 mg, and may be administered, i.e., 1–3 times daily, to yield levels of about 0.5–50 mg/kg, for adults.

Pharmaceutical compositions adapted for oral or parenteral administration, comprising an amount of one or more topical anesthetics compounds of formula (I) effective to treat mammalian conditions associated with pathological cellular proliferation, particularly human cancers, such as solid tumors and leukemias, are a preferred embodiment of the invention.

The ability of a compound to modulate the activity of PKCδ can be determined using assays that are known in the art. For example 1) a PKC translocation assay can be used to measure PKC activation; 2) the anti-phospho-PKCδ antibody can be utilized to assay for activation of the enzyme by detecting phosphorylation on threonine 505; and 3) a kinase assay can be utilized, in which PKCδ is immunoprecipitated and subsequently used with a target that it will phosphorylate.

Because of their ability to modulate PKCδ topical anesthetics are useful for treating diseases or conditions wherein PKCδ activity is implicated and wherein modulation of PKCδ is desirable. For example, compounds of the invention are useful for treating a disease or condition characterized by the pathological proliferation of mammalian cells, such as for example, human cancers, such as solid tumors and leukemias. Compounds of the invention are also be useful for treating autoimmune diseases, ischemia (e.g. myocardial ischemia), and restenosis following a revasculation procedure such as angioplasty.

As discussed above, U.S. Pat. Nos. 5,510,339 and 5,631,267 disclose the use of topical anesthetics to treat bronchial asthma and other eosinophil associated hypersensitivity diseases. Accordingly the therapeutic methods of the invention preferably exclude the treatment of bronchial asthma and other eosinophil associated hypersensitivity diseases as described in these patents.

Additionally, U.S. patent application Ser. No. 08/985,613 discloses the use of a sulfonylurea receptor (SUR) binding agent to treat IL-5 mediated pathologies. Thus, preferred topical anesthetics useful in the methods of the invention are not sulfonylurea binding agents.

U.S. patent application Ser. No. 08/985,613 also discloses a method for treating a disease mediated by IL-5 with an agent that is able to modify (e.g. block) ATP-dependent potassium channels, or a protein with which an ATP-dependent potassium channel interacts (such as a SUR). Thus, preferred topical anesthetics useful in the methods of the invention are agents that are not able to modify (e.g. block) ATP-dependent potassium channels, or a protein with which an ATP-dependent potassium channel interacts (such as a SUR), as described therein.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A therapeutic method for treating a disease or condition characterized by the pathological proliferation of mammalian cells, comprising administering to a mammal in need of such therapy, an amount of a topical anesthetic, or a pharmaceutically acceptable salt thereof, effective to treat the disease or condition.

2. The method of claim 1 wherein the disease or condition is cancer.

3. The method of claim 1 wherein the disease or condition is a solid tumor or leukemia.

4. A therapeutic method for treating an autoimmune disease comprising administering to a mammal in need of such therapy, an amount of a topical anesthetic, or a pharmaceutically acceptable salt thereof, effective to treat the autoimmune disease.

5. A method to inhibit the activity of PKCδ in vitro comprising contacting PKCδ with an effective inhibitory amount of a topical anesthetic; or a salt thereof.

6. A therapeutic method for inhibiting the activity of PKCδ in a mammal in need of such therapy comprising administering to the mammal, an effective PKCδ inhibitory amount of a topical anesthetic; or a pharmaceutically acceptable salt thereof.

7. A method for treating a condition or disease in a mammal wherein the activity of PKCδ is implicated and antagonism of its action is desired comprising administering to the mammal, an amount of a topical anesthetic, or a pharmaceutically acceptable salt thereof, effective to inhibit PKCδ and treat the condition or disease.

8. The method of claim 7 wherein the condition or disease is ischemia.

9. The method of any one of claims 1–8 wherein the topical anesthetic is an N-arylamide or carboxamide.

10. The method of any one of claims 1–8 wherein the topical anesthetic is lidocaine.

11. The method of any one of claims 1–8 wherein the topical anesthetic is an aminoalkylbenzoate.

12. The method of any one of claims 1–8 wherein the topical anesthetic is procaine, benoxinate or proparacaine.

13. The method of any one of claims 1–8 wherein the topical anesthetic is lidocaine, bupivacaine, mepivacaine, chloroprocaine, procaine, etidocaine, tetracaine, benoxinate, proparacaine, dibucaine, dyclonine, isobucaine, meprylcaine, piperocaine, prilocaine, propoxycaine, pyrrocaine, butacaine, cyclomethylcaine, dimethyisoquin, diperodon, hexylcaine, proparacaine, cocaine or a cocaine analog.

14. The method of claim 1 or 7 wherein the disease is not bronchial asthma or another eosinophil associated hypersensitivity disease.

15. The method of any one of claims 1–8 wherein the topical anesthetic is not a sulfonylurea receptor (SUR) binding agent.

16. The method of any one of claims 1–8 wherein the topical anesthetic does not modify an ATP-dependent potassium channel, or a protein with which an ATP-dependent potassium channel interacts.

* * * * *

UNITED STATES PATENT AND TRADEMARK OFFICE
CERTIFICATE OF CORRECTION

PATENT NO. : 6,391,888 B1
DATED : May 21, 2002
INVENTOR(S) : Gerald J. Gleich, Jennifer L. Bankers-Fulbright and Scott O'Grady It is certified that error appears in the above-identified patent and that said Letters Patent is hereby corrected as shown below:

<u>Title page,</u>
Item [56], OTHER PUBLICATIONS, "Shaub, R.G., et al" reference delete "339" and insert -- 399 --, therefor.

Signed and Sealed this

Fourth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,391,888 B1
DATED : May 21, 2002
INVENTOR(S) : Gerald J. Gleich, Jennifer L. Bankers-Fulbright and Scott O'Grady It is certified that error appears in the above-identified patent and that said Letters Patent is hereby corrected as shown below:

Title page,
Item [12], delete "Gleich" and insert -- Gleich et al. --.
Item [75], Inventor, delete "Gerald J. Gleich, Rochester, MN (US)" and insert the following:
-- Gerald J. Gleich, Rochester, Jennifer L. Bankers-Fulbright, Rochester, Scott O'Grady, White Bear Lake, all of MN (US) --.

Signed and Sealed this

Twenty-seventh Day of July, 2004

JON W. DUDAS
*Acting Director of the United States Patent and Trademark Office*